United States Patent [19]

Mrozik et al.

[11] Patent Number: 4,547,491
[45] Date of Patent: Oct. 15, 1985

[54] C-8A-OXO-AVERMECTIN AND MILBEMYCIN DERIVATIVES, PHARMACEUTICAL COMPOSITIONS AND METHOD OF USE

[75] Inventors: Helmut H. Mrozik, Matawan; Frank S. Waksmunski, South River, both of N.J.

[73] Assignee: Merck & Co., Inc., Rahway, N.J.

[21] Appl. No.: 632,094

[22] Filed: Jul. 18, 1984

[51] Int. Cl.[4] .................... A61K 31/70; C07H 17/08; C07D 493/22
[52] U.S. Cl. ...................... 514/30; 536/7.1; 549/265
[58] Field of Search ........................ 424/180; 536/7.1; 549/264, 265

[56] References Cited

U.S. PATENT DOCUMENTS

| | | | |
|---|---|---|---|
| 4,199,569 | 4/1980 | Chabala et al. | 536/7.1 |
| 4,200,581 | 4/1980 | Fisher et al. | 536/7.1 |
| 4,289,760 | 9/1981 | Mrozik et al. | 549/264 |
| 4,423,209 | 12/1983 | Mrozik et al. | 536/7.1 |
| 4,427,663 | 1/1984 | Mrozik | 536/7.1 |

Primary Examiner—Johnnie R. Brown
Attorney, Agent, or Firm—David L. Rose; Michael C. Sudol, Jr.; Mario A. Monaco

[57] ABSTRACT

There are disclosed novel avermectin and milbemycin compounds wherein the 8a position is oxidized to a ketone group. The 8a-oxo compounds are prepared by oxidizing an avermectin or milbemycin compound. The avermectin and milbemycin 8a-oxo compounds have utility as anti-parasitic agents and compositions for that use are also disclosed. The compounds are also highly potent insecticides against agricultural pests.

18 Claims, No Drawings

C-8A-OXO-AVERMECTIN AND MILBEMYCIN DERIVATIVES, PHARMACEUTICAL COMPOSITIONS AND METHOD OF USE

BACKGROUND OF THE INVENTION

The term avermectin (previously referred to as C-076) is used to describe a series of compounds isolated from the fermentation broth of an avermectin producing strain of Streptomyces avermitilis and derivatives thereof. The morphological characteristics of the culture are completely described in U.S. Pat. No. 4,310,519. The avermectin compounds are a series of macrolides, each of which is substituted thereon at the 13-position with a 4'-(α-L-oleandrosyl)-α-L-oleandrose group. The avermectin compounds and the instant derivatives thereof have a very high degree of anthelmintic and anti-parasitic activity.

The avermectic series of compounds isolated from the fermentation broth have the following structure:

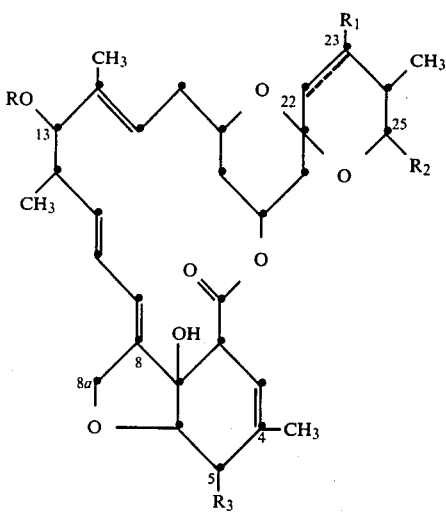

wherein R is the 4'-(α-1-oleandrosyl)-α-1-oleandrose group of the structure:

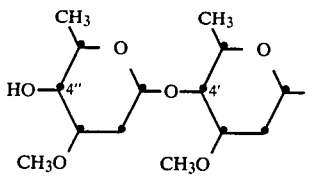

and wherein the broken line indicates a single or a double bond; $R_1$ is hydroxy and is present only when said broken line indicates a single bond;

$R_2$ is iso-propyl or sec-butyl; and $R_3$ is methoxy or hydroxy.

There are eight different major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'(α-L-oleandrosyl)-α-L-oleandrose):

| | $R_1$ (22,23-bond) | $R_2$ | $R_3$ |
|---|---|---|---|
| A1a | (Double Bond) | sec-butyl | —OCH$_3$ |
| A1b | (Double Bond) | iso-propyl | —OCH$_3$ |
| A2a | —OH | sec-butyl | —OCH$_3$ |
| A2B | —OH | iso-propyl | —OCH$_3$ |
| B1a | (Double Bond) | sec-butyl | —OH |
| B1b | (Double Bond) | iso-propyl | —OH |
| B2a | —OH | sec-butyl | —OH |
| B2b | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

Hydrogenation at the 22,23-double bond of avermectin B1a and/or B1b or deoxygenation of the 23-hydroxy group of avermectin B2a and/or B2b gives 22,23-dihydro avermectin B1a and/or B1b, a mixture of which is known as ivermectin. Derivatives of these dihydro compounds are also used as starting materials for this invention.

Milbemycin compounds are similar to the above avermectin compounds in that the 16-membered macrocyclic ring is present. However, such compounds have no substitution at the 13-position and have a methyl or ethyl group at the 25-position (the position of the $R_2$ group as found in the above structure). To the extent that such milbemycin compounds have retained the furan ring containing the 8a carbon atoms, they are to be construed as being within the ambit of this invention. Such milbemycin compounds and the fermentation conditions used to prepare them are described in U.S. Pat. No. 3,950,360. In addition, 13-deoxy-avermectin aglycones are prepared synthetically from the avermectin natural products and are disclosed in U.S. Pat. Nos. 4,171,134 and 4,173,571. Such compounds are very similar to the milbemycins differing from some of the milbemycins in having an isopropyl or sec butyl rather than a methyl or ethyl group at the 25-position.

SUMMARY OF THE INVENTION

The instant invention is concerned with certain derivatives of avermectin and milbemycin compounds wherein the 8a carbon atom is oxidized to the keto group. Thus it is an object of the instant invention to describe such avermectin and milbemycin 8a-oxo derivatives. A further object is to describe processes for the preparation of such compounds. A still further object is to describe the uses of such compounds as anti-parasitic agents. Still further objects will become apparent from a reading of the following description.

DESCRIPTION OF THE INVENTION

The compounds of the instant invention have the following structural formula.

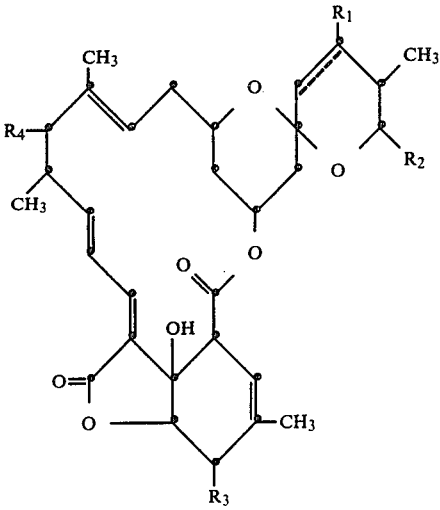

III wherein the broken line indicates a single or double bond;

$R_1$ is H, =O, loweralkanoyloxy, or OH provided that $R_1$ is present only when the broken line indicates a single bond;

$R_2$ is methyl, ethyl, isopropyl or sec-butyl;

$R_3$ is OH, $OCH_3$ or loweralkanoyloxy;

$R_4$ is H, OH, loweralkanoyloxy, α-L-oleandrosyloxy, α-L-oleandrosyl-α-L-oleandrosyloxy, 4'-loweralkanoyl-α-L-oleandrosyloxy, or 4''-loweralkanoyl-4'-α-L-oleandrosyl-α-L-oleandrosyloxy; and the tri-(loweralkyl)silyl protected hydroxy derivatives thereof.

The term "loweralkyl" when used in the instant application is intended to represent those alkyl groups either straight or branched chain which have from 1–5 carbon atoms. Examples of such alkyl groups are methyl, ethyl, propyl, iso-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propionyl, butyryl, valeryl, and the like.

The term "halogen" is intended to include those halogen atoms fluorine, chlorine, bromine and iodine.

Examples of preferred compounds of the instant invention, and their physiologically acceptable salts, are:
8a-oxo-avermectin B1a/B1b;
22,23-Dihydro-8a-oxo-avermectin B1a/B1b;
22,23-Dihydro-4'',5-bisphenoxyacetyl-8a-oxo-avermectin B1a/B1b.

The avermectin "b" compounds, those with a 25-isopropyl group, are difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b and the like. If desired, the pure "a" (25-sec-butyl) and "b" (25-isopropyl) compounds can be obtained by chromatographic separation, such as with reversed phase, high performance liquid chromatography.

The compounds of this invention are prepared by oxidizing the appropriate starting material with an oxidizing agent preferably pyridinium dichromate. The reaction is carried out on a starting material such as the natural product avermectin compounds or on an appropriately substituted derivative thereof. Readily oxidizable groups such as secondary alcohol groups must be protected during the oxidation using any of the many alcohol protecting groups known to those skilled in the art. Alternatively, the 8a-oxo reaction product may be further reacted to change the substituted at sites other than the 8a position.

The reaction is carried out in a solvent which is non-reactive to the effects of the oxidizing reagent. Solvents such as N,N-dimethylformamide, tetrahydrofuran, and the like are suitable.

The reaction is generally carried out at room temperature for from 12 to 48 hours, although temperatures of from 0° to 35° C. are suitable. Generally, the oxidizing reagent is utilized in an excess over the starting material. A molar excess of from 1 to 20 is acceptable and generally a molar excess of about 10 is employed. The product is isolated using techniques known to those skilled in the art.

PREPARATION OF STARTING MATERIALS

The ultimate starting materials for the compounds of this invention are the avermectin and milbemycin fermentation products defined above. Thus it is apparent that additional reactions are required to prepare many of the starting materials for the instant compounds. Specifically, reactions are carried out at the 4', 4'', 4a, 5, 13, 22, and 23-positions. It is often necessary or desirable to protect hydroxy groups which are not intended for reaction, with the appropriate protecting groups known in the art. Other reactions may then be carried out without affecting the remainder of the molecule. Subsequently, the protecting group is removed and the unprotected product isolated. The protecting group employed is ideally one which may be readily synthesized, will not be affected by the reaction being carried out, and may be readily removed without affecting any other functions of the molecule. It is noted that the instant protected compounds are novel and have considerable antiparasitic activity. They are included within the ambit of the instant invention. One preferred type of protecting group for the avermectin and milbemycin type of molecule is the tri-substituted silyl group, preferably the trialkyl silyl group. One especially preferred example, is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions.

If it is desired to protect the 23-hydroxy group a 4'',5,23-tri-(phenoxyacetyl) derivative can be prepared. Mild basic hydrolysis will leave the highy hindered 23-O-substituent but will hydrolize the 5- and 4''-O-phenoxy acetyl groups leaving them available for reaction. The 5-position may then be selectively protected as described above with t-butyldimethylsilyl, and the 4" group may then be reacted.

The silyl group may be removed after the other contemplated reactions may be carried out. The silyl group or groups are removed by stirring the silyl compound in methanol catalized by a catalytic amount of an acid, preferably a sulfonic acid such as p-toluene sulfonic acid. The reaction is complete in about 1 to 12 hours at from 0° to 50° C.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the avermectin A1 and B1-series of compounds. Thus in the "1" series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

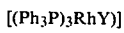

$[(Ph_3P)_3RhY)]$ wherein

Ph is phenyl and Y is halogen. The reduction procedure is completely described in U.S. Pat. No. 4,199,569 to Chabala et al.

Additional reactions which may be carried out to prepare the compounds of this invention are the selective removal of one or both of the α-L-oleandrosyl moieties (described in U.S. Pat. No. 4,206,205 to Mrozik et al.) or the selective acylation of the susceptible hydroxy groups (described in U.S. Pat. No. 4,201,861 to Mrozik et al.).

The reaction conditions which are generally applicable to the preparation of both the monosaccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 0.01 to 10% by volume. The reaction mixture is generally stirred at about 20°-40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the monosaccharide and the aglycone. The procedure for the preparation of the monosaccharide uses 1% concentrated sulfuric acid by volume in isopropanol at from 20°-40° C., preferably room temperature, for from 6 to 24 hours. For the preparation of the aglycone, 1% concentrated sulfuric acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acylated compounds are prepared using acylation techniques in which the reaction conditions will vary, depending upon the reactivity of the hydroxy group being acylated. Where there is more than one hydroxy group to be acylated, different reaction conditions are employed to minimize the formation of mixtures. The acylation reactions are described completely in U.S. Pat. No. 4,201,861 to Mrozik et al.

The acylation reagents employed are generally the halide, preferably the chloride, of the above loweralkanoyl groups. That is the loweralkanoyl halide reagent is generally employed.

In addition, the acylation reagent could be in the form of the anhydride. In the case of reactions carried out with the halide reagents, it is often advantageous to include in the reaction mixture a basic compound capable of reacting with and neutralizing the hydrogen halide which is liberated during the course of the reaction. Tertiary amines are preferred such as triethylamine, pyridine, dimethylamino pyridine, diisopropyl ethyl amine and the like. The basic compound is required in equimolar amounts relative to the numbered moles of hydrogen halide being liberated, however excess amounts, even using the basic compound as a solvent, are not detrimental.

In the case of the A1 compounds of avermectin, or of the hydrogenated avermectin A1 compounds there is only a single hydroxy group, 4" hydroxy, which may be acylated. The formation of the monosaccharide or the aglycone still leaves only a single hydroxy group which may be acylated, that is the 4' or 13 hydroxy group respectively.

In the case of the 4", 4' and 13 hydroxy groups of avermectin A1 compounds, the acylating reagent is dissolved in a suitable solvent, pyridine is preferred, and the acylating reagent added. The reaction is maintained at from 0° C. to room temperature for from 4 to 24 hours. The product is isolated using known techniques.

The A2 compounds have two available hydroxy groups, the 4"(4' or 13) or the 23 positions. The different hydroxy groups may be selectively acylated by controlling the reaction conditions.

The 4"(4' or 13) monoacyl compound may be prepared by using the reaction conditions described above for the A1 compound. Since the 23 hydroxy is less reactive than the 4"(4' or 13) position, mild reaction conditions (0° C.) will afford predominantly the monoacyl compound. Heating the reaction mixture at from room temperature to 100° C. for from 1 to 24 hours will produce the 4″(4′ or 13), 23-diacyl compound. If the 23 monoacyl compound is desired, the diacyl compound is treated with aqueous base, such as sodium hydroxide, at room temperature for from 1 to 24 hours. The 4″(4′ or 13) acyl group will be hydrolyzed leaving the 23 monoacyl compound.

The B1 compounds have 2 available hydroxy groups: at the 4″(4′ or 13) and the 5-positions. However, the two hydroxy groups have similar reactivities towards acetic anhydride in pyridine. When the reaction of the acylating agent in pyridine is carried out at about room temperature for from 4 to 24 hours, the diacyl compound is recovered. When the reaction is carried out at 0° C. a mixture of the 4″(4′ or 13) and 5 monoacyl compounds are recovered. To recover individual compounds, the mixture is placed on a chromatographic column or a preparative layer chromatographic plate of alumina or silica gel and the individual compounds are readily isolated. In addition, techniques such as high pressure liquid chromatography may be employed to separate mixtures of acylated compounds.

The B2 compounds have three hydroxy groups available for substitution: the 4″(4′ or 13), 5 and 23 positions. The relative reactivity of the various hydroxy groups is the same as in the other series of compounds. Thus, the triacyl compound may be prepared by carrying out the reaction at from room temperature to 100° C. The 4″(4′ or 13), 5 diacyl compound may be prepared by carrying out the reaction at no more than room temperature. At 0° C. a mixture of 4″(4′ or 13), and 5 monoacyl compounds is recovered which is separable as described above. By varying the reaction conditions and sequence, and by hydrolyzing the undesired acyl groups, all combinations of mono and diacyl compound may be recovered. For example, to prepare the 23-acyl compound, the triacyl compound is hydrolyzed with aqueous base as described above to remove the 4″(4′ or 13) and 5 acyl groups. Acylation of the 23 monoacyl compound at 0° C. will result in a mixture of the diacyl compounds which is readily separable.

The compounds wherein $R_4$ is hydrogen are prepared from the avermectin starting materials as described hereinbelow. The reaction at the 13-position can generally be carried either before or after the other above described reactions.

The series of reactions at the 13-position commences with the removal of the α-L-oleandrosyl-α-L-oleandrose side chain as described above. The avermectin aglycone compounds are then halogenated with a suitably reactive benzenesulfonyl chloride or bromide in the presence of a base to produce the "13-deoxy-13-halo-avermectin-aglycone" compounds. The halogen is then removed in a reaction with a trialkyltinhydride to produce the "13-deoxyavermectin aglycone compounds." The procedures for the preparation of the 13-deoxy compounds are described in detail in U.S. Pat. Nos. 4,171,134 and 4,173,571 to Chabala et al.

The 23-hydroxy group is oxidized to the 23-keto group to form the compounds wherein $R_1$ is =O, using oxidizing agents such as pyridinium dichromate; oxalylchloride-dimethylsulfoxide; acetic anhydride-dimethylsulfoxide; chromic acid-dimethylpyrazole; chromic acid; trifluoromethylacetic anhydride-dimethylsulfoxide; chromic acid-acetic acid; and the like. Oxalylchloride-dimethylsulfoxide is the preferred oxidizing agent. Suitably protected compounds, as described below, are employed. The reaction is carried out at from dry-ice bath temperatures to room temperature, preferably from dry-ice bath temperatures to 0° C. and is complete in from 1-24 hours. The reaction may be carried out in any solvent in which the starting materials are reasonably soluble, and which will not react with the oxidizing agent. Such solvents as dimethylformamide, dimethylsulfoxide, methylene chloride, chloroform, carbon tetrachloride and the like are acceptable. For pyridinium dichromate reactions, dimethylformamide and dimethylsulfoxide are preferred. For chromic acid-dimethylpyrazole reactions, methylene chloride is preferred. The compounds are isolated from the reaction mixture using procedures known to those skilled in the art.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasties of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parastic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

In the isolation of the avermectin compounds, which serve as starting materials for the instant proceses, from the fermentation broth, the various avermectin compounds will be found to have been prepared in unequal amounts. In particular an "a" series compound may be obtained in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a small percent by weight, and this structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

EXAMPLE 1

8a-Oxo-7-O-trimethylsilyl-22,23-dihydro avermectin B1a/B1b

10 Mg (0.0092 mmoles) of 4",5,7-O-tris-(trimethylsilyl)22,23-dihydro-avermectin B1a/B1b is suspended in 0.5 ml of dry dimethylformamide and with stirring at room temperature is combined with 34.6 mg (0.092 mmoles) of pyridinium dichromate. The reaction mixture is stirred at room temperature for 22.5 hours. The reaction mixture is diluted with water and extracted three times with ether. The combined ether extracts are washed with water, saturated sodium chloride solution, dried and evaporated to dryness in vacuo affording 7.8 mg of a glass material. The glass is purified on a preparative layer chromatography plate eluting with 10% tetrahydrofuran and 0.3% ethanol and methylene chloride. The product band is located under ultraviolet light and removed from the plate using the developing solvent system. The solvent is removed affording a glass which is identified as 8a-keto-7-O-trimethylsilyl-22,23-dihydro-avermectin B1a/B1b.

EXAMPLE 2

4",5-Di-O-t-butyldimethlysilyl-8a-oxo-22,23-dihydroavermectin B1a/B1b

55 Mg (0.050 mmoles) of 4",5-di-O-t-butyldimethylsilyl-22,23-dihydro-avermectin B1a/B1b dissolved in 2.5 ml of dry dimethylformamide is combined with 188 mg (0.50 mmoles) of pyridinium dichromate and the reaction mixture is stirred at room temperature for 19 hours. Then an additional 188 mg (0.50 mmoles) of pyridinium dichromate is added and stirring continued at room temperature for an additional 23 hours. The reaction mixture is diluted with ice water to a total volume of 25 ml and extracted four times with ether. The combined ether extracts are washed three times with water, once with saturated sodium chloride solution, dried and evaporated to dryness in vacuo affording a dark glass. The glass is purified using preparative layer chromatography on two 500μ plates eluted with 5% ethyl acetate in methylene chloride. The product is located under ultraviolet light and the material removed using 10% methanol in methylene chloride. The solvent is removed affording a tan glass. The product is identified by 300 MHz nuclear magnetic resonance as 4",5-di-O-t-butyldimethylsilyl-8a-oxo-22,23-dihydro-avermectin B1a/B1b.

EXAMPLE 3

5-O-t-Butyldimethylsilyl-8a-oxo-22,23-dihydroavermectin B1a/B1b

50 Mg (0.05 mmoles) of 5-O-t-butyldimethylsilyl-22,23-dihydro-avermectin B1a/B1b was dissolved in 2.5 ml of dry dimethylformamide and combined with 188 mg (0.5 mmoles) of pyridinium dichromate. The reaction mixture was stirred at room temperature for 19 hours whereupon an additional 188 mg (0.5 mmoles) of pyridinium dichromate was added and stirring continued at room temperature for another 24 hours. The reaction mixture was diluted with 25 ml of water and extracted five times with ether, washed three times with water, once with saturated sodium chloride solution, dried over magnesium sulfate and evaporated to dryness in vacuo affording 27.8 mg of a glass. The glass was purified on two 500μ preparative layer chromatography plates eluting with 20% ethyl acetate in methylene chloride. The product was located under ultraviolet light and removed from the plate using ethyl acetate affording 6.7 mg of product identified using 300 MHz nuclear magnetic resonance and mass spectrometry as 5-O-t-butyldimethylsilyl-8a-oxo-22,23-dihydro-avermectin B1a/B1b.

EXAMPLE 4

8a-Oxo-22,23-dihydro-avermectin B1a/B1b 8.2 Mg of 5-O-t-butyldimethylsilyl-8a-oxo-22,23-dihydro-avermectin B1a/B1b was dissolved in 1.5 ml of 1% solution of para-toluene sulfonic acid in methanol and left to stand at room temperature for 15 minutes. The reaction mixture was diluted with 10 ml of ice water containing 0.5 ml of saturated sodium bicarbonate solution. The aqueous mixture was extracted four times with ether and the combined organic phases washed four times with water, once with saturated sodium chloride solution, dried and evaporated to dryness in vacuo affording 6.8 mg of a glass. The glass was purified on a single preparative layer chromatography plate, 250μ thick, eluting with 10% tetrahydrofuran, 0.3% ethanol in methylene chloride. Four bands were identified under ultraviolet light and isolated separately from the plate using 10% methanol in methylene chloride. The products identified were 1.4 mg of 5-O-t-butyldimethylsilyl-8a-oxo-22,23-dihydro-avermectin B1a/B1b monosaccharide; 1.6 mg of 5-O-t-butyldimethylsilyl-8a-oxo-22,23-dihydro-avermectin B1a/B1b; 0.2 mg of 8a-oxo-22,23-dihydro-avermectin B1a/B1b monosaccharide; and 0.9 mg of 8a-oxo-22,23-dihydro-avermectin B1a/B1b.

EXAMPLE 5

4″,5-Di-O-phenoxyacetyl-22,23-dihydro-avermectin B1a/B1b

1 Gram (1.14 mmoles) of 22,23-dihydro-avermectin B1a/B1b was dissolved in 10 ml dry methylene chloride and 0.25 ml (3.08 mmoles, 243 mg) of dry pyridine added. The reaction mixture was cooled to 0° C. under a blanket of nitrogen and a solution of 0.39 ml (2.80 mmoles, 478 mg) of phenoxyacetyl chloride in 10 ml of dry methylene chloride was added dropwise over a period of 45 minutes. The reaction mixture was stirred for an additional 30 minutes and an additional 0.13 ml (1.54 mmoles) of pyridine and a solution of 0.2 ml (1.40 mmoles) of phenoxyacetyl chloride in 5 ml of dry methylene chloride added dropwise over 10 minutes. The reaction mixture was stirred an additional 30 minutes, and diluted with ice water to a volume of 100 ml with vigorous stirring. The phases were separated and the aqueous layer extracted three times with ether. The combined organic phases were washed three times with water, once with saturated sodium chloride, dried over magnesium sulfate and concentrated to dryness in vacuo affording 1.59 g of a light yellow foam. The product was chromatographed on 100 g of silica gel eluting with 10% ethyl acetate in methylene chloride for fractions 1 to 70 (taking 16 ml fractions) and 45% ethyl acetate in methylene chloride for fractions 71–131 (taking 20 ml fractions). The product was found in fractions 26–60 which afford 879 mg of a white foam which was identified by 300 MHz nuclear magnetic resonance and mass spectrometry as 4″,5-di-O-phenoxyacetyl-22,23-dihydro-avermectin B1a/B1b.

EXAMPLE 6

4″,5-Di-O-phenoxyacetyl-8a-oxo-22,23-dihydro-avermectin B1a/B1b 57.1 Mg (0.05 mmoles) of 4″,5-di-O-phenoxyacetyl-22,23-dihydro-avermectin B1a/B1b was dissolved in 2.5 ml of dry dimethylformamide and 188 mg (0.5 mmoles) of pyridinium dichromate was added in one portion and the reaction mixture was stirred for 20 hours whereupon an additional 188 mg (0.5 mmoles) of pyridinium dichromate was added and the reaction mixture stirred an additional 24 hours. The reaction mixture was diluted with water to a volume of 25 ml and extracted five times with ether. The combined organic layers are washed five times with water, once with saturated sodium chloride, dried over magnesium sulfate, evaporated to dryness in vacuo affording 26.7 mg of a light yellow glass. The glass was purified by preparative layer chromatography using two 500μ silica gel plates eluted with 5% tetrahydrofuran, 0.15% ethanol and methylene chloride. The product was recovered by extraction of the major band with 10% methanol in methylene chloride. The solution was evaporated to dryness in vacuo affording 17.2 mg of a yellowish foam which was identified by its nuclear magnetic resonance spectrum as 4″,5-di-O-phenoxyacetyl-8a-oxo-22,23-dihydro-avermectin B1a/B1b.

EXAMPLE 7

4″,5-di-O-phenoxyacetyl-8a-oxo-avermectin B1a/B1b

114 Mg (0.1 mmoles) of 4″,5-di-O-phenoxyacetyl-avermectin B1a/B1b is dissolved in 2.5 ml of dry dimethylformamide and combined with 188 mg (0.5 mmoles) of pyridinium dichromate. The reaction mixture is worked up as in Example 6 to 80 mg of a colorless glass which is purified by preparative layer chromatography on two 1000μ silica gel plates eluting with 5% ethyl acetate and methylene chloride affording material identified by nuclear magnetic resonance as 4″,5-di-O-phenoxyacetyl-8a-oxo-avermectin B1a/B1b.

EXAMPLE 8

5-O-tert-Butyldimethylsilyl-8a-oxo-22,23-dihydro-avermectin B1a/B1b

200 Mg of 5-O-t-butyldimethylsilyl-22,23-dihydro-avermectin B1a/B1b was dissolved in 4 ml of dry dimethylformamide and combined with 200 mg of pyridinium dichromate. The reaction mixture was stirred for 24 hours and an additional 200 mg of pyridinium dichromate was added and the reaction mixture stirred an additional 4 days. The reaction mixture was worked up as in Example 6 affording a white foam which was placed on two 1000μ preparative layer chromatography plates and eluted with an 8:2 mixture of cyclohexane:acetone affording three bands of material. The slowest band was identified by its nuclear magnetic resonance spectrum as 5-O-t-butyldimethyl-silyl-8a-oxo-22,23-dihydro-avermectin B1a/B1b.

EXAMPLE 9

8a-Oxo-22,23-dihydro-avermectin B1a/B1b

10 Mg of 5-O-t-butyldimethylsilyl-8a-oxo-22,23-dihydro-avermectin B1a/B1b was dissolved in 1 ml of methanol and stirred at room temperature. 20 Mg of para-toluene sulfonic acid hydrate was added and the reaction mixture stirred for 60 minutes. 8.5 Ml of ethyl acetate was added and the mixture washed with 2 ml of water and 0.5 ml of saturated sodium bicarbonate solution. The washings were repeated using the same volumes of solution. The organic layer was then washed twice with water and dried over magnesium sulfate and evaporated to dryness under a stream of nitrogen affording 7.0 mg of a glass. The glass was purified on a preparative layer chromatography plate, 250μ thick, eluting with a 90:10:0.3 mixture of methylene chloride, tetrahydrofuran and ethanol. The slowest moving band of 0.5 mg was identified as 8a-oxo-22,23-dihydro-avermectin B1a/B1b.

EXAMPLE 10

5-O-tert-Butyldimethylsilyl-8a-oxo-22,23-dihydro-13-deoxy-avermectin B1a/B1b aglycone When 142 mg. of 5-O-tert-butyldimethylsilyl-13-deoxy-22,23,-dihydro-avermectin B1a/B1b aglycone are reacted according to the procedure of Example 8, one obtains 5-O-tert-butyldimethylsilyl-8a-oxo-22,23-dihydro-13-deoxy-avermectin B1a/B1b aglycone.

EXAMPLE 11

13-Deoxy-22-,23-dihydro-8a-oxo-avermectin B1a/B1b aglycone

When 7 mg of 5-O-tert-butyldimethylsilyl-13-deoxy-22,23-dihydro-8a-oxo-avermectin B1a/B1b aglycone are reacted according to the procedure of example 9, 13-deoxy-22-23-dihydro-8a-oxo-avermectin B1a/B1b aglycone is obtained.

What is claimed is:

1. A compound having the formula:

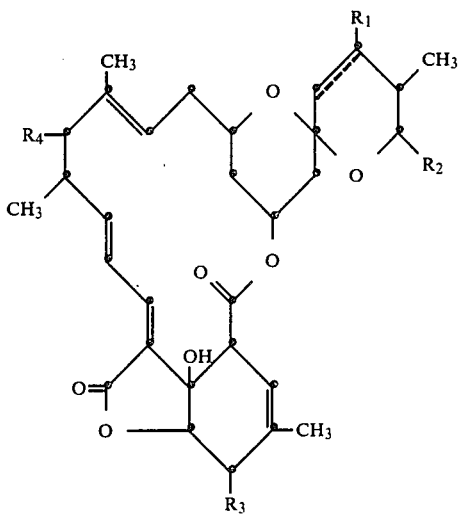

wherein the broken line indicates a single or a double bond; wherein $R_1$ is H, loweralkanoyloxy, —OH or =O provided that $R_1$ is present only when the broken line indicates a single bond;

$R_2$ is methyl, ethyl, isopropyl or sec-butyl;

$R_3$ is OH, OCH$_3$ or loweralkanoyloxy;

$R_4$ is H, —OH, loweralkanoyloxy, α-L-oleandrosyloxy, 4'-(α-L-oleandrosyl)-α-L-oleandrosyloxy, 4'-loweralkanoyl-α-L-oleandrosyloxy, or 4"-loweralkanoyl-4'-(α-L-oleandrosyl)-α-L-oleandrosyloxy; and the tri(-loweralkyl)silyl protected hydroxy derivatives thereof.

2. The compound of claim 1 which is 22,23-dihydro-8a-oxo-avermectin B1a and B1b.

3. The compound of claim 1 which is 22,23-dihydro-4",5-bisphenoxyacetyl-8a-oxo-avermectin B1a and B1b.

4. The compound of claim 1 which is 8a-oxo-avermectin A1a and A1b.

5. The compound of claim 1 which is 8a-oxo-avermectin A2a and A2b.

6. The compound of claim 1 which is 8a-oxo-avermectin B1a and B1b.

7. The compound of claim 1 which is 8a-oxo-avermectin B2a and B2b.

8. The compound of claim 1 wherein $R_4$ is 8α-L-oleandrosyloxy.

9. The compound of claim 8 which is 8a-oxo-22,23-dihydro-avermectin B1a and B1b monosaccharide.

10. The compound of claim 1 wherein $R_4$ is hydrogen.

11. The compound of claim 10 which is 8a-oxo-milbemycin $\alpha_1$ and $\alpha_3$.

12. The compound of claim 10 which is 8a-oxo-13-deoxy-22,23-dihydro-avermectin B1a and B1b aglycone.

13. The compound of claim 1 wherein $R_4$ is —OH.

14. The compound of claim 13 which is 8a-oxo-22,23-dihydro-avermectin B1a and B1b aglycone.

15. A method for the treatment of parasitic infections which comprises administering to an animal infected with parasites an effective amount of a compound of claim 1.

16. A composition useful for treating animals infected with parasites which comprises an inert carrier and an effective amount of a compound of claim 1.

17. A method for the treatment of insect infestations which comprises treating the area of such insect infestation with an effective amount of a compound of claim 1.

18. A composition useful for treating areas of insect infestations which comprises an inert carrier and an effective amount of a compound of claim 1.

* * * * *

UNITED STATES PATENT AND TRADEMARK OFFICE
CERTIFICATE OF CORRECTION

PATENT NO. : 4,547,491
DATED : October 15, 1985
INVENTOR(S) : HELMUT H. MROZIK et al.

It is certified that error appears in the above—identified patent and that said Letters Patent is hereby corrected as shown below:

In Claim 8 "8α" should be --α--

Signed and Sealed this

Twenty-ninth Day of July 1986

[SEAL]

Attest:

Attesting Officer

DONALD J. QUIGG

Commissioner of Patents and Trademarks